United States Patent [19]

Ismail et al.

[11] Patent Number: 4,683,209
[45] Date of Patent: Jul. 28, 1987

[54] VIABILITY TEST DEVICE

[75] Inventors: Ibrahim A. Ismail, Mishawaka; Paul Hemmes; Mark T. Skarstedt, both of Elkhart; Adam Zipp, Goshen, all of Ind.

[73] Assignee: Miles Laboratories, Inc., Elkhart, Ind.

[21] Appl. No.: 887,723

[22] Filed: Jul. 21, 1986

Related U.S. Application Data

[62] Division of Ser. No. 705,711, Feb. 26, 1985, Pat. No. 4,649,121.

[51] Int. Cl.⁴ ............................................. G01N 31/00
[52] U.S. Cl. .......................................... 436/14; 436/8; 435/14
[58] Field of Search .......................... 435/14; 436/8–18

[56] References Cited

U.S. PATENT DOCUMENTS 4,193,766 3/1980 Daunora et al. ...................... 436/18

Primary Examiner—Deborah L. Kyle
Assistant Examiner—T. J. Wallen
Attorney, Agent, or Firm—Mary G. Boguslaski

[57] ABSTRACT

A viability test device wherein the viability of a test composition for the determination of an analyte of interest can be determined by simply wetting the device with ordinary water. The viability device can be prepared in three formats: a control or calibrator device, an internal control device and a self indicating device. Unreacted analyte, or an analog thereof, can be incorporated in a limited defined portion of a dried carrier matrix incorporated with a test composition to provide an internal control test device. When wetted with water, a positive optical response, usually color, indicates the test composition can provide a viable test for the analyte. The internal control test device is particularly advantageously used by diabetics in their own homes where a negative test response could be due to the desired control of the user's condition or due to deterioration of a test composition because of unfavorable storage conditions.

6 Claims, 2 Drawing Figures

4,683,209

VIABILITY TEST DEVICE

This is a division of application Ser. No. 705,711, filed Feb. 26, 1985, now U.S. Pat. No. 4,649,121.

FIELD OF THE INVENTION

The invention relates in general to unitary solid state test devices and, in particular, to diagnostic test devices containing unreacted analyte, or an analog thereof, incorporated with a carrier matrix containing a test composition reactive with the analyte.

UTILITY

Solid state unitary test devices useful for the determination of a variety of analytes of diagnostic interest are widely used in hospitals, clinical laboratories and in the physicians' office. After manufacture, these test devices are packaged and shipped away from the manufacturers' controlled storage facilities. Each package can then be subjected to different stress conditions, such as heat, humidity and light, which can adversely affect the viability of the test composition. It is therefore desirable to have a test device which can be conveniently tested by the user to determine if the test composition still provides a positive test for the analyte in question. Since glucose testing is often done at home by relatively untrained persons, it is particularly desirable to have a glucose test device which provides the user with a test for the viability of the test composition.

INFORMATION DISCLOSURE

The viability of test compositions incorporated with diagnostic test devices has previously been checked with a separately provided control composition. The control composition contains the analyte which is reactive with the test composition or an analyte analog which reacts readily with water to produce the analyte (e.g., very easily hydrolyzed esters of the reactive analyte or its analog). The control composition can be available in a liquid form, ready for use, or in a powder form which, when dissolved in a predetermined quantity of water, forms a control solution of known concentration. U.S. Pat. No. 3,920,580 is exemplary of liquid control solutions useful to determine the viability of solid state test devices.

Also available are control test devices wherein a carrier matrix is incorporated with the control composition. The control device delivers a known quantity of analyte, or analog thereof, into a predetermined quantity of water, or appropriate solvent, to form a control solution of known concentration. An example of such a control test device is illustrated in U.S. Pat. No. 4,234,316.

U.S. Pat. No. 4,365,970 discloses a specimen test slide and method for testing occult blood. The test slide is designed for use with fecal samples. The slide is composed of front and rear panels covering a sheet of paper impregnated with guaiac indicator. At some distance from the panel opening designed for the application of sample, there is a control area composed of a positive and negative monitor for hemoglobin. The positive monitor is an area impregnated with hemin, the reactive portion of the hemoglobin which is the analyte of interest. The negative monitor is a defined area of the guaiac impregnated paper which is not intended to come into contact with sample. Once sample has been applied to the test slide, the test paper is developed with a peroxide solution. The positive monitor should develop a blue color and the negative monitor should remain colorless; variation from this pattern indicates some deterioration of the guaiac impregnated paper. The guaiac impregnated paper will not provide a detectable response when contacted with water in the presence of the analyte. Neither the indicator impregnated paper nor the portion of the indicator paper incorporated additionally with hemin is capable of providing a detectable response when simply wetted with water.

DESCRIPTION OF THE DRAWINGS

FIG. 1a depicts internal control devices in two configurations after wetting with water devoid of the analyte. FIG. 1b shows the same devices after contact with a sample containing an analyte concentration which provides a detectable response greater than that provided by the analyte concentration incorporated with the matrix. If the detectable response is visible, the appearance of the internal control portion of the matrix (shown dotted) is then indistinguishable from the appearance of the whole carrier matrix.

In FIGS. 2a–c, the analyte incorporated area is visible as it would be if the detectable response was color and the device had been wetted with water devoid of the analyte. FIGS. 2a and 2b show different possible configurations where a single carrier is incorporated with unreacted analyte at different concentrations and in different patterns on the test composition incorporated carrier matrix. FIG. 2c show multiple carriers affixed to a single support member, each carrying an internal control portion of unreacted analyte at a different concentration. In 2c, the analyte is incorporated in the shape of a number. FIG. 2d depicts the device of 2c after contact with a sample containing an analyte concentration which provides a detectable response greater than that provided by the analyte concentration incorporated into control area 3, but less than that provided by the concentration of analyte incorporated with control area 4. If the detectable response is color, control area 4 is visually distinguishable from the background response developed, within the normal read time for the test device, in the rest of the matrix.

SUMMARY OF THE INVENTION

Figure 1:
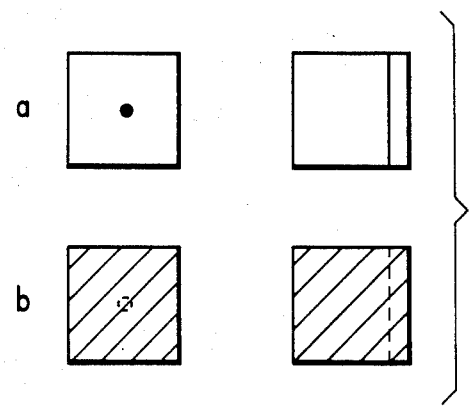
FIG. 1 shows two of the possible configurations for a viability test device useful as an internal control device.
Figure 2:
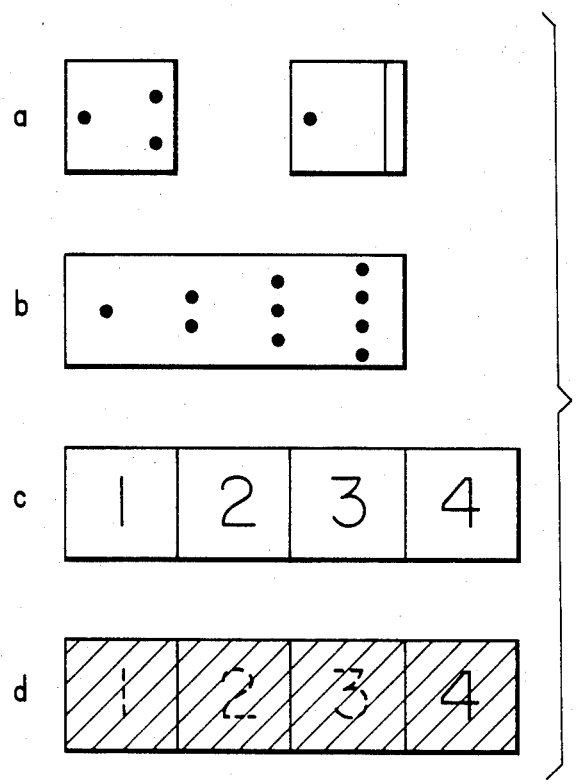
FIG. 2 shows some possible configurations for a self indicating device.

The invention provides a solid state unitary test device, useful for determining the viability of a test composition incorporated therein, comprising: (a) a carrier matrix; (b) a test composition for the determination of an analyte, incorporated substantially uniformly with the carrier matrix, which test composition is capable of providing a detectable optical response upon wetting of the carrier matrix with water in the presence of the analyte to be determined; and (c) unreacted analyte, or analog thereof incorporated in at least a portion of the test composition incorporated carrier matrix, at a concentration sufficient to provide a detectable optical response in the doubly incorporated carrier matrix upon wetting of the matrix with water.

The viability test device can be provided as a control device when the unreacted analyte is incorporated substantially uniformly with the entire test composition incorporated matrix. When the unreacted analyte is incorporated with a limited defined portion of the test composition incorporated carrier, the viability device becomes an internal control device. The internal control device is capable of providing a detectable optical response when wetted with water, indicating the viability of the incorporated test composition. The internal control area does not interfere with the use of such a device in the determination of the analyte in an aqueous fluid sample. By incorporating the unreacted analyte, or analog thereof, at different concentrations in a plurality of limited defined portions of the test composition incorporated matrix, a self indicating device can be provided. The incorporated analyte concentrations can be chosen to be clinically significant concentrations of the analyte. A self indicating device can also be provided by attaching a plurality of internal control devices, each incorporated with a different incorporated analyte concentration, to a support member.

In particular, one embodiment of the invention provides an internal control and self indicating device for the determination of glucose. Such a device is especially useful to the large number of diabetic patients who test their urine glucose at home daily.

DETAILED DESCRIPTION OF THE INVENTION

Commercially available test devices are intended as single use, throw-away devices. While most such devices are designed for use with a particular body fluid sample such as urine, blood, serum, saliva, or cerebrospinal fluids, any aqueous test sample can be tested. The same is true of the devices of the present invention.

Testing of a single viability test device by wetting with water indicates the viability of the test composition incorporated therein and is expected to indicate the viability of other test devices in the consumer's hands which have been stored under the same or similar conditions. For example, testing of a viability test device taken from a bottle of similar devices stored in a bathroom medicine cabinet, if positive, would indicate the viability of the other test devices in the bottle. Those other devices, if of the internal control or self indicating type, can be used to determine the concentration of analyte in an aqueous fluid sample.

According to the present invention, a viability test device can be prepared by incorporating unreacted analyte, or an analog thereof, with a carrier matrix which has been incorporated with a test composition reactive with the analyte of interest. The viability test device can be prepared in three formats depending on the area incorporated with unreacted analyte, the concentration of unreacted analyte and the configuration or number of the analyte incorporated matrices used for a single device. The viability test device indicates the viability of the test composition when a detectable response is produced when the device is wetted by ordinary water or any aqueous fluid devoid of the analyte of interest. If the test composition has deteriorated so that it is unable to produce a response to the analyte, there will be no detectable response when the device is wetted with water. The presence of this detectable response is a positive indication that the test device, and indeed any test device stored with it, can provide a viable test for the analyte. When a home user contacts a sample with a diagnostic test device, the preferred "normal" indication is often a negative or "devoid of analyte" response. This is particularly true with diabetics where normal urine glucose concentrations should be very low. At present, the home user is left to wonder if the sample was truly negative, as desired, or if the diagnostic test device had deteriorated due to storage conditions and no longer provides a detectable response.

A. FORMATS

1. Control Device

The viability test device can be prepared as a control device by incorporating substantially the entire test composition incorporated carrier with the unreacted analyte, or analog thereof. Such a test device can be included in a bottle or lot of purchased ordinary diagnostic test devices containing only the test composition, which will be stored under similar conditions by the ultimate consumer. Testing of that control test device by contacting it with water and observing the detectable response visually or instrumentally assures the user that other strips, purchased at the same time and stored under similar conditions, will provide a viable test for the analyte of interest.

2. Internal Control Device

A particularly convenient format for the viability test device is that of an internal control device, wherein the unreacted analyte or an analog thereof, is incorporated with a limited defined portion of the test composition incorporated carrier. The user can be assured that the strip provides a viable test for the analyte since a detectable response is produced in a defined limited portion of the device even when wetted by a negative sample if the test composition is viable. An internal control test device can be used as a diagnostic test device since the incorporated analyte, or analyte analog, does not interfere with the ability of the device to assay an aqueous test sample.

3. Self-Indicating Device

A self indicating test device can also be prepared according to the present invention. A test composition incorporated carrier can be incorporated with the analyte, or analog thereof, at one or more concentrations, in separated defined portions of the carrier. Although the self-indicating device can act as a viability test device, it can provide a great deal more information. When contacted by a test sample containing the analyte, the concentration range of the analyte can be determined by comparing the detectable response produced in substantially the entire device with the response in the areas incorporated with analyte, or its analog. The self indicating device is particularly useful when the detectable optical response is color so that the responses can be determined visually. Such a device can be advantageously used to allow immediate recognition of the normal clinical range of the analyte.

A self indicating device can also be prepared by utilizing multiple internal control matrices affixed to a single support member. Unreacted analyte can be incorporated with a limited defined area of each matrix, at a different concentration level. When the device is contacted with a test sample, the concentration level of the sample can be estimated to be between the highest incorporated analyte concentration in which detectable response in the control area is substantially indistinguishable from the rest of the reacted matrix and incorporated analyte concentration of the matrix in which the control area detectable response is distinguishable from the background detectable response.

A. Analyte

There are many diagnostic analytes which are tested for routinely in clinical laboratories. In general these include body analytes, microorganisms, toxins and drugs. Body analytes of interest include cholesterol and triglycerides, white blood cells, red blood cells, ketones, urea, uric acid, proteins and glucose. The presence of an over abundance of any of these analytes in certain body fluids is indicative of anomalous body function. Likewise the presence or absence of certain enzymes normally found in the body can be used as an indication of anomalous body function. Common enzyme analytes include lactate dehydrogenase; creatinine kinase, glutamic oxalacetic transaminase and glutamic pyruvic transaminase. It is also becoming increasingly common to test for body levels of certain therapeutic drugs such as theophylline, phenobarbital and lithium, and drugs of abuse such as morphine, heroin and marijuana.

In addition to analytes of interest in the medical sphere, other analytes such as toxins and fertilizer components are of particular interest for environmental testing. A viability test device has particular utility when testing is sporadic and/or test devices are carried for long periods under less than ideal storage conditions.

B. Particular Analytes

Although broad classes of analytes can be determined with solid state unitary test devices and can be incorporated with such test devices to form viability test devices, diagnostic test devices for body fluid analytes are those most prevalent and hence are those used in the examples herein. For example, a common diagnostic test is the determination of the glucose level in blood or urine. Presently available glucose test devices are based on a test composition including glucose oxidase and an indicator system such as peroxidase and a chromogenic indicator. Since glucose oxidase is reactive only with a particular form of glucose, $\beta$-D glucose, the viability test device must incorporate this form, or an analog thereof, as the analyte, or glucose must be incorporated in a manner which permits mutarotation to the required form. If a mixture of $\alpha$- and $\beta$-D-glucose is incorporated in solution or suspension, care must be taken to choose a solvent which allows the necessary mutarotation or supports the $\beta$ form. Suitable solvents include dimethylformamide, pyridine, 2-methoxyethanol and methoxy-2-propanol.

C. Optical Response

The unreacted analyte, or analog thereof, must be incorporated with the carrier matrix at a concentration sufficient to provide a detectable optical response when the device is wetted with tap water or distilled water devoid of the analyte.

The detectable response can be fluorescent or color. The form of the optical response is dependent on the reaction mechanism of the test composition and not on the analyte incorporated therein. In a preferred embodiment, the optical response is color which can be detected in the device visually or by reflectance reading with a spectrophotometer such as the Ames SERALYZER® reflectance photometer available from Miles Laboratories, Inc., Elkhart, Ind.

Test devices designed to determine a particular analyte are often based on kinetic reactions where a colorimetric endpoint is determined a specified time after contact with the sample. That time, called the normal read time for the test device herein, is usually chosen at a time point which provides the greatest color differentiation between concentration levels of sample analyte which the device is designed to determine. The incorporated unreacted analyte in this invention should provide a detectable optical response within the normal read time for the test composition incorporated carrier. For example, glucose test devices presently available have a normal read time of less than about 2 minutes, preferably 1 minute or less.

D. Carrier Matrix

The carrier matrix can be any substance capable of being incorporated with the components of the test composition, as long as it is substantially inert with respect to the test composition, porous and/or absorbent relative to the aqueous sample to be tested. The expression "carrier matrix" refers to either bibulous or nonbibulous matrices which are insoluble in and maintain their structural integrity when exposed to water or to other physiological fluids. Suitable bibulous matrices which can be used include paper, cellulose wood, synthetic resin fleeces, woven and nonwoven fabrics and the like. Nonbibulous matrices includes glass fiber, polymer films, preformed or microporous membranes and organoplastic materials such as polypropylene and the like.

It is therefore to be appreciated that in producing a test device of the invention all such carrier matrix concepts can be employed, as can others. The matrix can include a system which physically entraps any or all of these ingredients, such as polymeric microcapsules which rupture upon contact with an aqueous solution. For example, the unreacted analyte can be maintained separately from the test composition within the same carrier matrix without interaction until contacted with an aqueous sample. The matrix can also comprise a layered system wherein each composition component is homogeneously combined in a fluid or semifluid state, which later hardens or sets, thereby entrapping the ingredients until wetted by the aqueous test sample. Other matrix formats are contemplated, including the use of a commercially available preformed porous membranes or microporous membranes formed by techniques such as phase inversion. Polymer film matrices such as films produced by latex formulations based on a latex polymer suspensions, for example the 60:40 copolymer of styrene and butadiene, or other natural or synthetic polymers or mixtures thereof. Examples of such film formulations can be found in 3,630,957 and 4,312,834, incorporated herein by reference.

A unitary solid state test strip or test device can be prepared by incorporation of a carrier matrix, with drying between incorporation steps. When a whole blood sample is tested, a test composition incorporated carrier can be coated to allow excess sample to be washed or wiped off prior to incorporation of the unreacted analyte.

Incorporation of the test composition can be accomplished by any method such as spreading, spraying or dipping, a process often called impregnation, which allows the carrier matrix to be incorporated with a viable test composition reactive with the analyte of interest.

E. Incorporation of the Analyte

The analyte, or analog thereof, which is reactive with the test composition can be incorporated with the test composition incorporated carrier matrix in any manner which will prevent premature interaction with the test composition, but allow substantially immediate interaction of the analyte and test composition once the carrier is wetted with water. This can be done in a number of ways including microencapsulation of the analyte and deposition onto the dried carrier previously incorporated with the test composition; commonly employed printing techniques such as jet printing; or by the controlled deposition of a solution or suspension of the analyte, or reactive analog, in a dried nonaqueous organic solvent. If the solution or suspension is incorporated substantially uniformily with the entire dried test composition incorporated carrier, a viability test device useful as a control or calibrator device is formed.

A viability test device useful as an internal control device can be formed by incorporating unreacted analyte, or an analog thereof with a limited defined portion of the dried test composition incorporated carrier. Incorporation can be accomplished by any of the methods mentioned above. While it was originally believed that the capillary action of a carrier, particularly a paper carrier, would spread the unreacted analyte over the whole matrix, it has been found that a solution or suspension can be controlled to allow incorporation with a limited defined area as desired. The solution or suspension can be placed onto the dried carrier with a syringe, pipette or similar device capable of delivering a controlled quantity of solution or suspension.

It is particularly preferred to incorporate the analyte, or analog thereof, in a solution, since the concentration of the analyte incorporated can be controlled more easily when a true solution is used. In either case, whether a solution or suspension is used, care must be taken to use nonaqueous organic solvents which are dried (i.e., free from any water). If water remains in the solvent, the test composition incorporated carrier could be wetted during the incorporation of the analyte causing premature interaction between the test composition and the analyte. Methods for drying organic solvents are well known to organic chemists.

The area of incorporation of the unreacted analyte can be any convenient geometric shape, for example half the matrix, a letter, or number or a dot. It is preferred that the internal control portion be a fine offset line or a small dot on the matrix in order that the optical response of the internal control not interfere with the optical response in the remainder of the device when the device is used with an aqueous fluid sample as a test for the determination of the analyte in question.

The concentration of incorporated unreacted analyte can be chosen as desired. It is preferred to chose a low concentration of analyte which will provide a detectable optical response when wetted with water, but which response becomes virtually indistinguishable from the test composition response upon contact with a sample containing an analyte concentration approximately the same or higher than the incorporated analyte concentration.

A self indicating device can be formed by incorporating two or more limited defined portions of a test composition incorporated carrier with different unreacted analyte concentrations. Practically, due to the size of the test devices normally employed, a single carrier matrix can preferably be incorporated with two different concentrations of unreacted analyte at different defined areas of the dried carrier. If more concentration markers are desired a large carrier can be used or multiple carriers, each incorporated with a different concentration of unreacted analyte, can be affixed to a support member to provide a unitary test device.

With an analyte of clinical interest it is particularly preferred that the optical response provided by the concentrations used correspond to the optical response of clinically significant concentrations, such as the high and low end of the so-called normal clinical range of the analyte; thus giving the user a fast, convenient indication that additional testing might be required. The concentration of the analyte must be carefully chosen to provide a detectable optical response equivalent to that seen in a clinical sample. This concentration can be determined experimentally and is usually very close to, but slightly less than, the sample analyte concentration desired.

For example, it can be desirable to have a self indicating device for urinary glucose prepared so that the user will know if the sample values obtained are within a specific range, for example 30 to 100 mg/dL. Commonly available glucose test devices are generally composed of a carrier matrix incorporated with glucose oxidase and an indicator system such as peroxidase and 3,3',5,5'-tetramethylbenzidine. The self indicating test device can be prepared by incorporating such a glucose test device with a low concentration of analyte which provides a detectable optical response when wetted with water. When a second device so constructed is contacted with a urine sample containing 30 milligrams per deciliter (mg/dL) glucose, the optical response is indistinguishable from the response in the entire device, within the normal read time for the test composition incorporated matrix. A second incorporated analyte concentration would provide a response which is detectable when wetted with water but which is indistinguishable from the response in the entire device in the normal read time, when a second device so constructed is contacted with sample which contains more than 100 mg/dL glucose. Therefore if both control areas are visible, the sample contains less than 30 mg/dL glucose; if one control area is visible, the sample contains a glucose concentration within the specified range; and if neither control area is visible, the sample contains a concentration of glucose above the specified range. In the latter case treatment and/or additional testing may be indicated.

Drying of the matrix after the incorporation of the unreacted analyte or analog thereof, can be accomplished by any means which will not deleteriously affect the incorporated unreacted analyte or test composition, usually by means of an air oven. The dried paper can thereafter be cut and mounted on one end of a support member, for example, a rigid or semirigid polystyrene film strip. Mounting of the paper on the strip can be accomplished through use of a double-faced adhesive tape, such as that commercially available from the 3M Company, St. Paul, Minn. as DOUBLE STICK ®. The support member provides a convenient handle which facilitates use of the test.

The following examples describe experiments which were performed in developing the present invention. While the examples serve to illustrate the invention, they are not to be interpreted as limiting its scope which is defined solely by the claims. One skilled in the art will be able to make such variations, substitutions and changes in the composition, ingredients and reaction parameters as may seem desirable.

F. Abbreviations

The following abbreviations are used in the examples:
mg—milligrams
dL—deciliter
μL—microliter
mg—milligrams
M—molar
d—density
g/cm³—grams per cubic centimeter
°C.—degrees centigrade
mg/dL—milligrams per deciliter.

EXAMPLE I

Internal Control Glucose Device

Glucose can be incorporated with a carrier matrix, previously incorporated with a glucose test composition, either as a solution or a suspension of glucose.

a. Suspension

Glucose was pulverized to a fine powder in a mortar. A mixture of hexane (density=0.66 g/cm³) and dibromomethane (density=2.50 g/cm³) was prepared which had nearly the same density as the glucose crystals. The crystals could then be suspended easily by hand on Vortex mixing to produce a suspension which settled very slowly, if at all. A 30 microliter (μL) sample of suspension was placed as a small dot with a pipette on a glucose test device designed for the determination of glucose in serum or whole blood. The glucose test device was a commercially available glucose SERALYZER ® reagent strip, marketed by Miles Laboratories, Inc., Elkhart, Ind., 46515 which comprises a paper matrix incorporated with a glucose reactive test composition: glucose oxidase, peroxidase and 3,3',5,5' tetramethylbenzidine. No visible change occurred when the unreacted analyte was incorporated. The analyte incorporated devices were then dried at 45° C. for six minutes in an air oven. Upon drying, the internal control area showed a visible colorimetric reaction when the device was wetted with 30 μL of ordinary water b. Solution

A paper carrier matrix was incorporated with a glucose test composition comprising glucose oxidase, peroxidase and 3,3',5,5'-tetramethylbenzidine, at levels designed for the determination of urine glucose and dried. A colorless solution containing about 100 mg/dL glucose in methoxy-2-propanol was applied to the dried carrier as a small dot in the center of the matrix with a syringe under air pressure, and the carrier was dried again. The glucose solution used gave a detectable optical response, when wetted by water, equivalent to the response in the whole matrix when a second device was contacted with a sample containing 100 mg/dL glucose. This concentration provided the development of color within 1 minute after the device was dipped in water, the normal read time for the glucose test device. When the device was dipped into an aqueous sample containing about 30 mg/dL glucose, the device showed an overall color, corresponding to the concentration of 30 mg/dL on the appropriate color chart, with a small dot of a darker color in the internal control area. This result would indicate to the user that the low reading is truly correct, not an aberration due to low reactivity of a test device in which the test composition has deteriorated due to storage conditions or other stress.

Similar results were obtained when a solution of glucose in pyridine was applied to a dried glucose test incorporated paper matrix with a pipette.

EXAMPLE II

Internal Control Urea Devices

Reagent grade guanidine hydrochloride, an analog of urea, is ground to a fine powder in a mortar and pestle. According to the *Merck Index* the density of solid guanidine hydrochloride is 1.32 g/cm³. Using the formula:

$$d_{Hexane}X_{hex} + d_{DDM}(1-X_{Hex}) = d_{solid}$$

where:
$d_{Hexane}$=density of hexane=0.669/cm³
$d_{DBM}$=density of dibromomethane=2.509/cm³
$X_{Hex}$=mole fraction of hexane in liquid mixture
the proportion of hexane in the hexane/dibromomethane mixture is calculated to equal the density of guanidine hydrochloride. A mixture of this composition is prepared and the guanidine suspended in it. A 30 μL aliquot of suspension is placed as a small dot on each of a number of SERALYZER ® Blood Urea Nitrogen (BUN) reagent strips with a pipette. The SERALYZER ® BUN test is a paper matrix incorporated with a test composition comprising ophthalaldehyde and an ion-exchange resin which produces a low pH when a sample containing sodium chloride is applied. The devices are then dried in an oven at 45° C. for about 6 minutes. The internal control dot of guanidine hydrochloride will turn dark blue green when the device is wetted with water.

EXAMPLE III

Internal Control Uric Acid Device CONTROL URIC ACID DEVICE

Uric acid obtained from Sigma Chemical Co., St. Louis, Mo. was reacted with approximately 0.1 M lithium hydroxide. The lithium salt of uric acid was crystallized from water by evaporation and dried in a desiccator for two days over silica gel. The dried lithium urate was ground finely and then was suspended in a hexane-dibromomethane mixture by the following procedure. Since the density of the analyte was unknown, some solid was added to dibromomethane. Hexane was then added dropwise until a solvent mixture was obtained in which the solid tended to suspend itself without floating or sinking. The resulting suspension (30 μL) was placed on SERALYZER ® uric acid reagent strips (available from Miles Laboratories, Inc., Elkhart, Ind. 46515) as a small dot with a pipette and dried in an oven at 45° for 6 minutes. The SERALYZER ® uric acid test is a paper matrix incorporated with a test composition reactive with uric acid comprising uricase, 4-aminoantipyrene, 3-methyl-2-benzothiazolinone and buffers. The resulting internal control area turned dark red when wetted with ordinary water. The uric acid analog, lithium urate, was used rather than the free acid because its higher solubility facilitated interaction of the control composition with the test composition when the device was wetted.

EXAMPLE IV

Internal Control Ketone Test Device

Methanol was predried for two days over molecular sieves (13X available from Alfa, Danvers, Miss.) and then filtered. The methanol was then used to prepare a solution 120 mg/dL sodium methylacetoacetate. A 0.5 μL aliquot of the methanol solution was pipetted onto a KETOSTIX® reagent strip commercially available from Miles Laboratories, Inc., Elkhart, Ind. KETOSTIX® is a paper matrix incorporated with a test composition comprising magnesium sulfate and sodium nitroprusside. The control area so introduced was in the form of a small dot. Devices incorporated in this manner were dried over molecular sieves. When contacted with ordinary water, the internal control area of the devices turned dark brown.

EXAMPLE V

Internal Control Bilirubin Device

Crystallized bilirubin was dissolved in predried chloroform (concentration of 1.60 mg/dL). A 1 μL portion of the solution was applied in a small dot with a pipette to the bilirubin reagent pads on N-MULTISTIX® SG reagent strip (available from Miles Laboratories, Inc., Elkhart, Ind. 46515). The bilirubin reagent pad is composed of a paper matrix incorporated with a test composition comprising buffered 2,4-dichloroaniline diazonium salt. The devices were dried. No color development was observed during and after application. When the internal control bilirubin device was wetted with ordinary water, a purple color developed in the internal control area.

EXAMPLE VI

Control or Calibrator Device

A lyophilized powdered form of glutamic oxalacetic transaminase (AST) can be obtained from Sigma Chemical Co., St. Louis, Mo. Samples of the powder containing 2000 units of enzyme would be suspended in a hexane-dibromomethane mixture whose specific gravity matches that of the enzyme using the procedure of Example III. A suspension containing 0.37 unit of enzyme per microliter of suspension is prepared. A 30 μL aliquot of the suspension is placed on a SERALYZER® AST reagent strip so that it substantially covers the whole matrix and then dried. (The SERALYZER® AST test consists of a paper matrix incorporated with a test composition comprising α-ketoglutarate, L-aspartate, potassium phosphate, magnesium chloride, thiamine pyrophosphate, 3,5-dichloro-2-hydroxybenzene sulfonate, 4-aminoantipyrine, oxalodecarboxylase, pyruvate oxidase, peroxidase and buffers). The amount of enzyme used corresponds to that in a serum sample containing 100 units of enzyme which has been diluted according to the SERALYZER® AST test procedure. The strip is then dried at 60° C. for about 6 minutes. When the strip is contacted with 30 μL of distilled water, color development is followed by using the SERALYZER® reflectance photometer available from Miles Laboratories, Inc. The instrument displays the value of 100 units at the end of the normal four minute read time for an AST strip. The strip thus prepared serves as a control strip for the diagnostic test device for AST and avoids the problem of reconstituting sera as a control.

EXAMPLE VII

Self Indicating Glucose Device

The VISIDEX® II reagent strips, commercially available from Miles Laboratories, Inc., Elkhart, Ind., are used to prepare a self indicating blood glucose device which indicates to the user when a sample glucose concentration is within the normal range. The extreme range of normal adult glucose is set at 60 mg/dL to 110 mg/dL in blood. (Jacobs D. S., Kasten, B. L., DeMott W. R., Wolfson, W. L. in Laboratory Test Handbook with DRG Index, Mosby/Lexi-Comp. St. Louis 1984). The VISIDEX® II reagent strip is composed of a paper matrix incorporated with a test composition comprising glucose oxidase, peroxidase, buffers and 3,3',5,5'-tetramethylbenzidine with a coating of ethylcellulose and gelatin.

One glucose solution is prepared in dried pyridine at a concentration which, when incorporated into the VISIDEX® II strip, dried and wetted with water, will produce a color virtually indistinguishable from that produced when an ordinary VISIDEX® II strip is contacted with a blood sample containing 60 mg/dL glucose and wiped for reading. A second glucose solution is prepared in dried pyridine at a concentration which, when incorporated into a VISIDEX® II strip dried and wetted with water, will give a detectable response, color, virtually indistinguishable from that produced when an ordinary VISIDEX® II strip is contacted with a blood sample containing 110 mg/dL glucose and wiped for reading. These concentrations are found by experimentation. One fine line of each solution is printed on the VISIDEX® II strip, preferably on opposite sides near the edges of the matrix.

When a drop of blood is placed on this strip and wiped off, following the VISIDEX® II directions, one of three cases can arise. In case I, a pale color can develop over the entire strip with two lines visible where the glucose was applied. This indicates that the sample contains glucose at a level significantly less than 60 mg/dL. This is a clinically dangerous level of hypoglycemia. In case II, a uniform color develops which is significantly darker than the line produced by the 60 mg/dL line but lighter than the 110 mg/dL line. Thus only one line is easily discerned visually. This would be the normal case indicating the presence of normal blood glucose levels. In case III, the color developed by the sample is so dark that neither line is visible. This corresponds to clinically elevated glucose levels. This method can be easily generalized to any number of lines, or patterns subject only to the ability to print the reagent lines and produce visually distinct patterns.

Obviously many modifications and variations of the disclosed devices can be made without departing from the spirit or scope of the invention.

What is claimed is:

1. A method for preparing a viability test device, comprising the sequential steps of:
   (a) incorporating a carrier matrix substantially uniformly with a test composition which test composition is capable of providing a detectable optical response upon wetting of the test composition incorporated carrier matrix with water in the presence of the analyte to be determined;
   (b) drying;
   (c) incorporating at least a portion of the dried carrier matrix with a solution of unreacted analyte, or analog thereof, in a dried non-aqueous solvent at a analyte concentration sufficient to provide a detectable optical response in the doubly incorporated carrier matrix upon wetting of the matrix with water; and (d) drying.

2. A method for preparing a viability test device, comprising the sequential steps of:
   (a) incorporating a carrier matrix substantially uniformly with a test composition which test composition is capable of providing a detectable optical response upon wetting of the test composition incorporated carrier matrix with water in the presence of the analyte to be determined;
   (b) drying;
   (c) incorporating at least a portion of the dried carrier matrix with a suspension of finely divided particles of unreacted analyte, or analog thereof, in a dried non-aqueous solvent; and
   (d) drying.

3. A method for preparing an internal control test device comprising the steps of:
   (a) incorporating a carrier matrix substantially uniformly with a test composition which test composition is capable of providing a detectable optical response upon wetting of the test composition incorporated carrier matrix with water in the presence of the analyte to be determined;
   (b) drying;
   (c) incorporating a limited defined portion of the dried carrier matrix with a solution of unreacted analyte, or analog thereof, in a dried non-aqueous solvent at an analyte concentration sufficient to provide a detectable optical response in the doubly incorporated carrier matrix upon wetting of the matrix with water; and
   (d) drying.

4. The method of claim 3 in which the incorporated analyte is chosen from a mixture of $\alpha$- and $\beta$-D-glucose, $\beta$-D-glucose or an analog of D-glucose, and which dried nonaqueous solvent used is capable of dissolving and maintaining D-glucose in the $\beta$ form or capable of supporting mutarotation of D-glucose to the $\beta$ form.

5. The method of claim 4 in which the solvent is chosen from dimethylformamide, pyridine, 2-methoxyethanol and methoxy-2-propanol.

6. A method for preparing internal control test device comprising the steps of:
   (a) incorporating a carrier matrix substantially uniformly with a test composition, which test composition is capable of providing a detectable optical response upon wetting of the test composition incorporated carrier matrix with water in the presence of the analyte to be determined;
   (b) drying;
   (c) incorporating a limited defined portion of the dried carrier matrix with a suspension of finely divided particles of unreacted analyte, or analog thereof, in a dried nonaqueous solvent at an analyte concentration sufficient to provide a detectable optical response in the doubly incorporated carrier matrix upon wetting of the matrix with water; and
   (d) drying.

* * * * *